(12) United States Patent
Pfaendner et al.

(10) Patent No.: US 10,364,340 B2
(45) Date of Patent: Jul. 30, 2019

(54) USE OF ORGANIC OXYIMIDES AS RADICAL GENERATORS IN PLASTICS, METHOD FOR GENERATING RADICALS IN PLASTICS AND USE OF SAID METHOD

(71) Applicant: FRAUNHOFER-GESELLSCHAFT ZUR FÖRDERUNG DER ANGEWANDTEN FORSCHUNG E.V., München (DE)

(72) Inventors: Rudolf Pfaendner, Rimbach (DE); Markus Mazurowski, Ginsheim-Gustav (DE)

(73) Assignee: Fraunhofer-Gesellschaft zur förderung der angewandten Forschung e.V., München (DE)

( * ) Notice: Subject to any disclaimer, the term of this patent is extended or adjusted under 35 U.S.C. 154(b) by 0 days.

(21) Appl. No.: 15/511,471

(22) PCT Filed: Sep. 16, 2015

(86) PCT No.: PCT/EP2015/071249
§ 371 (c)(1),
(2) Date: Mar. 15, 2017

(87) PCT Pub. No.: WO2016/042038
PCT Pub. Date: Mar. 24, 2016

(65) Prior Publication Data
US 2017/0260363 A1  Sep. 14, 2017

(30) Foreign Application Priority Data
Sep. 18, 2014  (DE) ........................ 10 2014 218 811

(51) Int. Cl.
| | | |
|---|---|---|
| C08K 5/5373 | (2006.01) | |
| B29C 48/00 | (2019.01) | |
| C08K 5/3417 | (2006.01) | |
| C07F 9/572 | (2006.01) | |
| C08K 5/5313 | (2006.01) | |
| C09D 5/18 | (2006.01) | |
| C09D 123/12 | (2006.01) | |
| C09K 15/30 | (2006.01) | |
| C09K 15/32 | (2006.01) | |
| C09K 21/12 | (2006.01) | |
| B29C 45/00 | (2006.01) | |
| B29K 23/00 | (2006.01) | |
| B29K 105/00 | (2006.01) | |

(52) U.S. Cl.
CPC ........ C08K 5/5373 (2013.01); B29C 45/0001 (2013.01); B29C 48/022 (2019.02); C07F 9/5728 (2013.01); C08K 5/3417 (2013.01); C08K 5/5313 (2013.01); C09D 5/18 (2013.01); C09D 123/12 (2013.01); C09K 15/30 (2013.01); C09K 15/322 (2013.01); C09K 21/12 (2013.01); B29K 2023/06 (2013.01); B29K 2023/12 (2013.01); B29K 2105/0005 (2013.01)

(58) Field of Classification Search
None
See application file for complete search history.

(56) References Cited

U.S. PATENT DOCUMENTS

| 4,267,084 A * | 5/1981 | Mizutani ................. C08L 27/06 524/527 |
| 4,409,367 A | 10/1983 | Beijleveld et al. |
| 9,428,692 B2 | 8/2016 | Okada et al. |
| 2008/0061270 A1 | 3/2008 | Tsuji et al. |
| 2008/0269383 A1* | 10/2008 | Pauquet ................. C08K 5/527 524/120 |
| 2009/0286060 A1* | 11/2009 | Sala ...................... C07D 209/48 428/220 |
| 2014/0225034 A1 | 8/2014 | Okada et al. |

FOREIGN PATENT DOCUMENTS

| CN | 1968744 A | 5/2007 |
| CN | 101258194 A | 9/2008 |
| CN | 103764259 A | 4/2014 |
| WO | WO 01/90113 A1 | 11/2001 |
| WO | WO 2006/106059 A1 | 10/2006 |
| WO | WO 2007/028731 A1 | 3/2007 |
| WO | WO 2008/101845 A1 | 8/2008 |

(Continued)

OTHER PUBLICATIONS

*Plastics Additives Handbook*, 5th edition, Hans Zweifel, Editor, Hanser Publishers, Munich, pp. 725-811 (2001).
Aubert et al., "Azoalkanes—novel flame retardants and their structure—property relationship," *Polym. Adv. Technol.* 22(11): 1529-1538 (2011).
Aubert et al., "Azoalkanes—A Novel Class of Additives for Cross-Linking and Controlled Degradation of Polyolefins," *Macromolecular Materials and Engineering*. 292: 707-714 (2007).
Pawelec et al., "Triazene compounds as a novel and effective class of flame retardants for polypropylene," *Polym. Degrad. Stab.* 87(6): 948-954 (2012).
European Patent Office, International Search Report and Written Opinion issued in International Application No. PCT/EP2015/071249 (dated Nov. 27, 2015).

(Continued)

*Primary Examiner* — Robert T Butcher
(74) *Attorney, Agent, or Firm* — Leydig, Voit & Mayer, Ltd.

(57) ABSTRACT

The present invention relates to the use of phosphorus-containing organic oxyimides according to the general formula I described below as flame retardant for plastic materials, as radical generators in plastic materials and/or as stabilizers for plastic materials. The present invention relates in addition to a flame-retardant plastic material molding compound in which the previously described phosphorus-containing organic oxyimides are integrated, and also to a method for the production of the previously mentioned plastic material composition. Furthermore, the present invention relates to a molded part, a paint or a coating made of the previously mentioned flame-retardant plastic material composition.

17 Claims, No Drawings

(56) References Cited

FOREIGN PATENT DOCUMENTS

| WO | WO 2012/000022 A1 | 1/2012 |
| WO | WO 2014/064064 A1 | 5/2014 |
| WO | WO 2014/154636 A1 | 10/2014 |
| WO | WO 2015/180888 A1 | 12/2015 |

OTHER PUBLICATIONS

International Bureau of WIPO, International Preliminary Report of Patentability issued in International Application No. PCT/EP2015/071249 (dated Mar. 21, 2017).
State Intellectual Property Office of the People's Republic of China, First Office Action in Chinese Patent Application No. 201580050105.0 (dated Jun. 21, 2018).
European Patent Office, Communication Pursuant to Article 94(3) EPC in European Patent Application No. 15 771 536.8 (dated Apr. 15, 2019).

* cited by examiner

USE OF ORGANIC OXYIMIDES AS RADICAL GENERATORS IN PLASTICS, METHOD FOR GENERATING RADICALS IN PLASTICS AND USE OF SAID METHOD

CROSS-REFERENCE TO RELATED APPLICATIONS

This patent application is the U.S. national phase of International Application No. PCT/EP2015/071249, filed on Sep. 16, 2015, which claims the benefit of German Patent Application No. 10 2014 218 811.3, filed Sep. 18, 2014, the disclosures of which are incorporated herein by reference in their entireties for all purposes.

The present invention relates to the use of organic oxyimides as radical generators in plastic materials. In addition, the present invention relates to a method for the generation of radicals in plastic materials, in particular for degradation- and crosslinking- and grafting reactions of plastic materials or polymers and also to a use of this method.

The controlled production of different types of polymers, in particular of types of polyolefins (different molecular weights, melting viscosities, molecular weight distributions, density) can, on the one hand, be effected during synthesis, but also in a subsequent step, e.g. during processing by means of extrusion or injection moulding. An established method is thereby addition of radical formers, which accordingly initiate radical reactions at the processing temperatures, which then lead, as a function of the polymer structure, to a polymer degradation, i.e. to a reduction in the molecular weight, or to a polymer increase, i.e. to an increase in the molecular weight up to branching and crosslinking.

A commercially important method is the degradation of polypropylene (so-called "vis-breaking") to form a product with a lower molecular weight and narrower molecular weight distribution (so-called "controlled rheology PP" or "CR-PP"). The resulting products are used e.g. for the production of polypropylene fibres ("melt-blown" or "spun-bonded" method) or for easily-flowing thin-walled injection moulded parts ("thin-wall injection moulding"). Conventional radical generators which are used for this method are organic peroxides (see e.g. D. Munteanu in H. Zweifel, Plastics Additives Handbook, Munich 2001, p. 725-811). Organic peroxides however require extensive safety devices during handling, lead to undesired secondary reactions, and the decomposition products from the peroxides can negatively influence the polymer properties, such as e.g. the long-term stability. The use of aqueous hydrogen peroxide (WO 2012/000022) thereby represents an improvement, however here the handling with respect to technical safety is likewise challenging and cannot be effected in the commonly available processing apparatus. Further known alternatives for radical generators in polypropylene degradation processes are hydroxypiperidine esters (WO 0190113), asymmetrical azo compounds (WO 2006/106059) or iminoxytriazines (WO 2014/064064). These compounds are however frequently difficult to access synthetically so that they are commercially unimportant.

A further industrially important process is crosslinking of polyethylene (e.g. LDPE, LLDPE, MDPE) with radical formers. These processes with addition of peroxides are used frequently in the production of pipes and cables. In addition, there applies in turn that the mentioned safety aspects must be taken into account, here uncontrolled secondary reactions lead to undesired gel formation and to processing problems.

A further industrially important process is grafting of monomers or unsaturated oligomers onto existing polymer chains in the presence of organic peroxides. These processes are important first and foremost for the production of maleic anhydride-grafted or acrylic acid-grafted polyethylene or polypropylene, polyolefin co- and terpolymers, and also maleic anhydride-grafted styrene-butadiene or styrene-butadiene-styrene block copolymers and the hydrated subsequent products thereof. Here also, as a consequence of the comparatively low decomposition temperatures of the peroxides, undesired secondary reactions, such as degradation, gel formation and/or discolouration, can occur.

There is therefore still a requirement for radical generators with improved control of the radical processes initiated herewith, an adjustable initiation temperature, high process safety and simple synthetic accessibility, which in addition can be used as additives on normal processing machines, such as extruders.

The object of the present invention is hence to indicate further radical generators for plastic materials which circumvent the previously mentioned problems.

This object is achieved by the features of the organic oxyimides used as radical generators in plastic materials described herein, by the features of the method for the generation of radicals in plastic materials described herein, and the advantageous developments thereof. Uses according to the invention are also described.

The present invention therefore relates to the use of organic oxyimides as radical generators in plastic materials. It is known according to the invention that the use of organic oxyimides, comprising at least one structural element of subsequently illustrated formula I

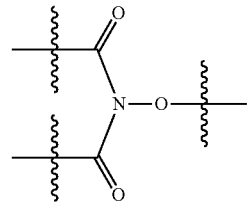

Formula I is suitable as radical generators in plastic materials.

Formula I should thereby be understood such that the illustrated structural element is contained in the organic oxyimide. The oxyimides used according to the invention should not thereby be equated with isocyanurates or compounds or classes of compounds derived herefrom.

According to a preferred embodiment of the invention, in particular oxyimides, comprising at least one structural element of following formula II

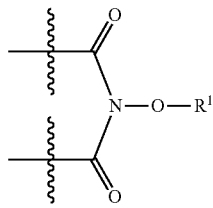

Formula II are used as radical generators for plastic materials, $R^1$ standing for hydrogen or a possibly substituted alkyl-, cycloalkyl-, aryl-, heteroaryl- or acyl-radical.

Alternatively, or in combination with the previously mentioned preferred variant, likewise bridged oxyimides, comprising at least one structural element of subsequent formula III are used

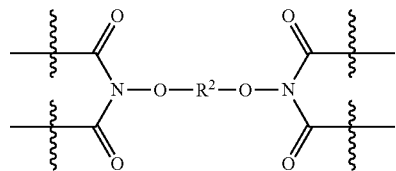

Formula III $R^2$ standing for a possibly substituted alkylene-, cycloalkylene-, arylene-, heteroarylene- or bridging acyl-radical.

The oxyimide used according to the present invention is thereby likewise preferably halogen-free, i.e. the corresponding compound does not comprise any halogen atoms.

According to a preferred variant, $R^2$ is selected from radicals of the group consisting of
—$(CH_2)_n$— with n=1 to 18, —$CH(CH_3)$—, —$C(CH_3)_2$—, —O—, —S—, —$SO_2$—, —NHCO—, —CO—, —OC(O)O— and also the subsequently illustrated groups

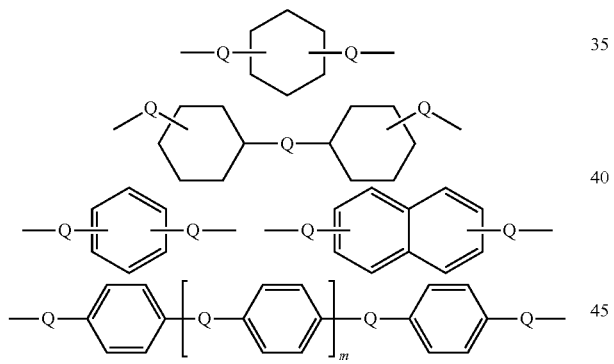

the cycloaliphatic or aromatic ring systems contained in the previously illustrated groups being unsubstituted or substituted by one or more alkyl- and/or alkoxy groups, Q upon each occurrence, being the same or different and being selected from the group consisting of a chemical bond and also the radicals —$(CH_2)_n$— with n=1 to 18, —$CH(CH_3)$—, —$C(CH_3)_2$—, —O—, —S—, —$SO_2$—, —NHCO—, O—C(O)—O—, —CO—, and m being 0 or 1 to 18.

For particular preference, the radicals $R_2$ are thereby reproduced by the subsequently illustrated structural elements, Q having the above-indicated meaning:

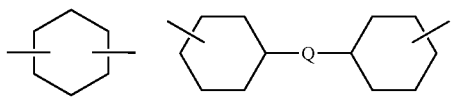

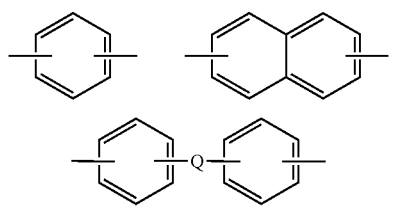

In particular, the radicals $R^2$ are thereby given by the subsequent structural elements:

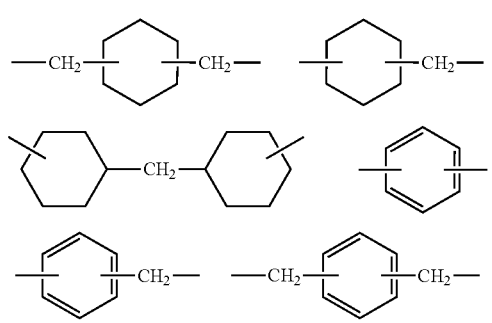

According to a particularly preferred embodiment, in the case of this variant of the invention, the organic oxyimide has one of the subsequent structural formulae:

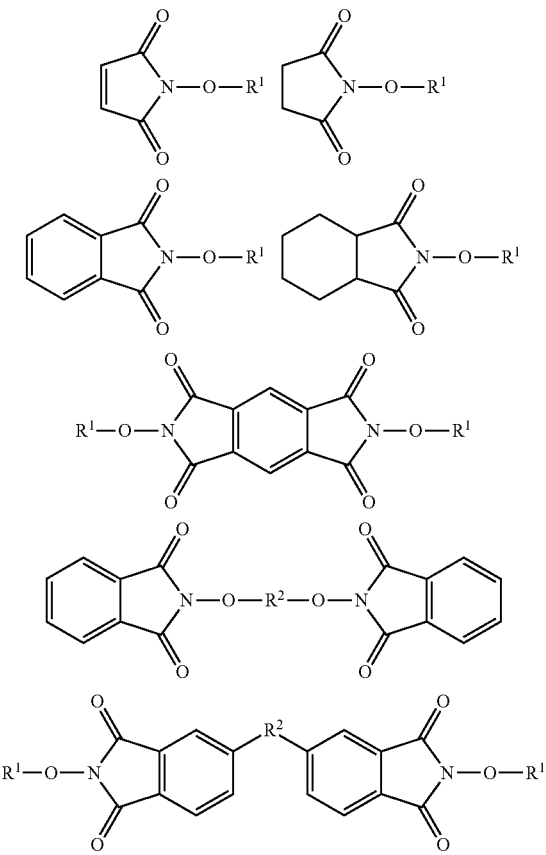

-continued

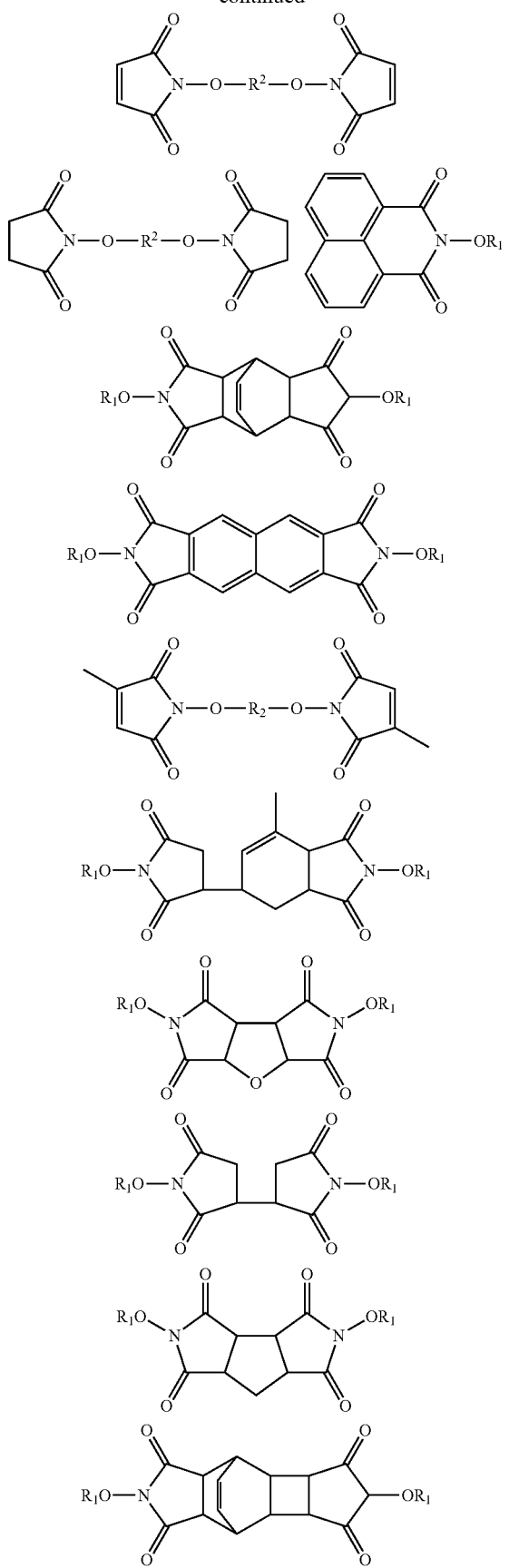

-continued

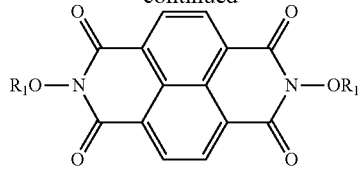

respectively R¹ and R² having the above-indicated meaning and R¹ and R₁ or R² and R₂ having the same meaning.

A particularly preferred radical R¹ is thereby hydrogen, an alkyl- or an acyl-radical.

As radical generators in plastic materials, the subsequently illustrated compounds are suitable in particular

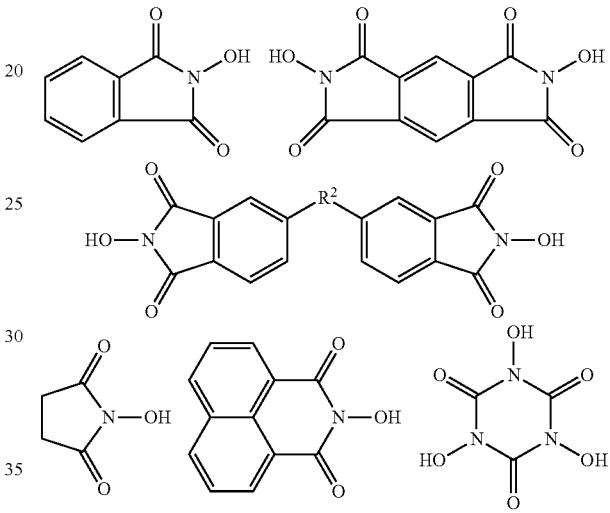

R² having the above-indicated meaning.

The selection of the suitable radical generator is thereby effected such that the formation of the radicals is effected at the processing temperatures of the respective polymers within a sufficient range for the reaction and the respective processing method. The temperatures at which a radical formation is effected can be determined, for example, by DSC ("Differential Scanning Calorimetry"). A further criterion for selection is the formation of reaction products, which can for example be volatile and hence can easily be removed from the product, or can be high-molecular and hence remain in the product without any disadvantages. The respective processing processes and temperatures for plastic material processing processes are known to the person skilled in the art. Plastic material processing processes and temperatures pertaining thereto can however also be deduced from the expert literature, such as e.g. H. Domininghaus, P. Elsner, P. Eyerer, T. Hirth, Kunststoffe (Plastic Materials), 8$^{th}$ edition, Springer 2012. In particular, for degradation methods, the further addition of chain transfer agents can be advantageous. Possible chain transfer agents can be selected from the class of thiols, disulfides, phosphoric acid esters, phosphines, organic halides, such as iodides, bromides, chlorides, acid esters, aldehydes or tertiary amines. Preferably, the chain transfer agents have a boiling point above the processing temperature of the respective polymer. Particularly preferred are sulphur derivatives, such as thiols and disulfides. Suitable chain transfer agents are for example:

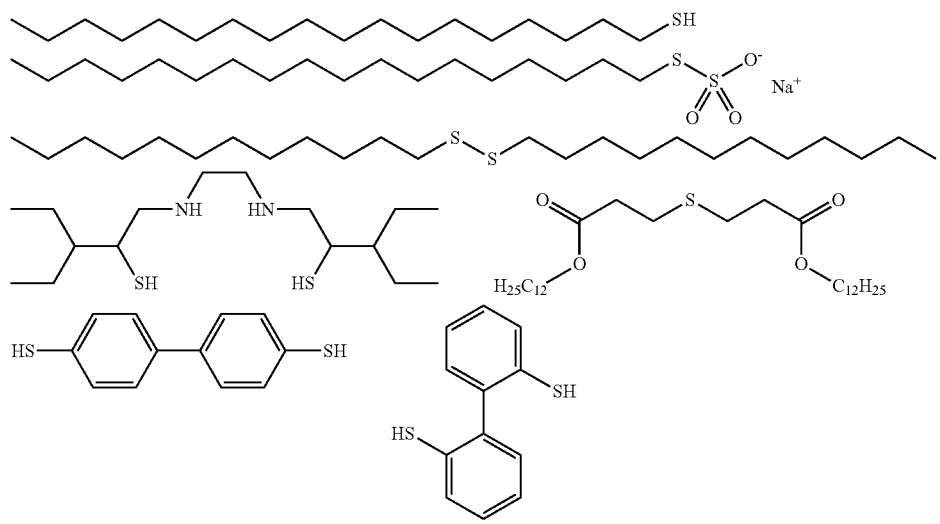

In particular for molecular weight increase reactions and for crosslinking reactions, the addition of further multifunctional compounds, in addition to the radical generator and to the polymer, can be advantageous. Suitable compounds include the classes of a) repeatedly unsaturated oligomers and polymers based on polybutadiene or polyisoprene
b) di- and polyvinyl compounds, such as e.g. divinyl benzene
c) di- and polyallyl compounds, such as e.g. polyallyl ether or polyallyl ester, trisallyl isocyanuranate, trisallyl cyanurate, diallyl bisphenol-A
d) di- and polymaleimides
e) di- and poly(meth)acrylester of di- and polyalcohols, and/or
f) organofunctional silanes Typical examples of organofunctional silanes are:

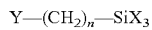

with n=0 to 3; Y=CH$_2$=CH—, CH$_2$=C(CH$_3$)COO—, NH$_2$—, SH—, Cl—; X=—OR (R=Me, Et), —OCOCH$_3$.

Typical examples of di- and polymaleimides are:

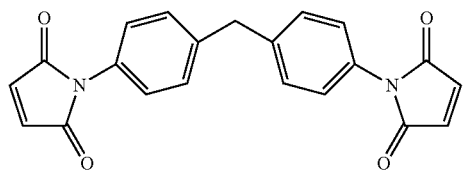

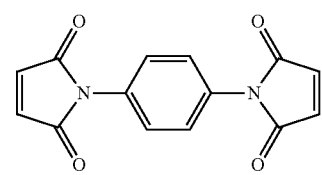

-continued

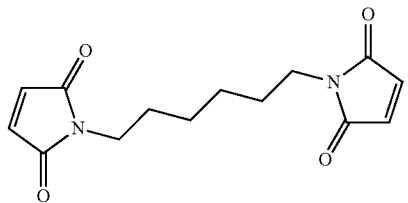

Typical examples of di- and poly(meth)acrylesters of di- and polyols are:

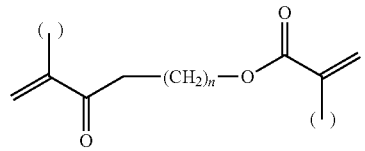

with n = 2-5

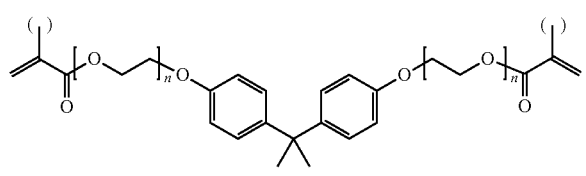

with n = 1-5

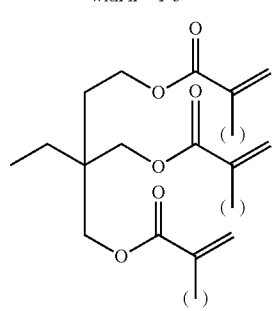

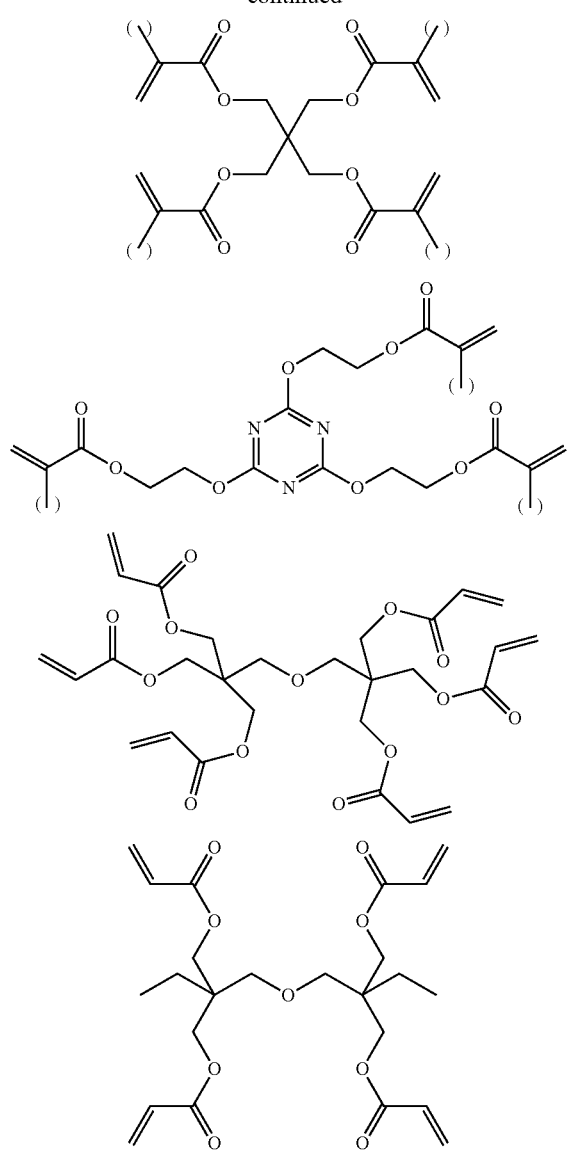

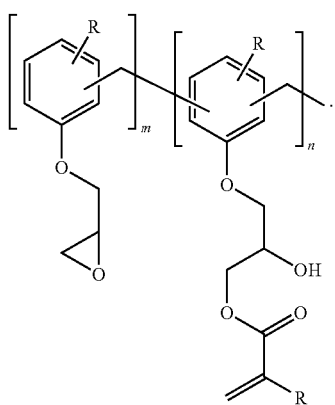

with R = H or methyl
and m = 0-10, n = 2-10

A typical example of an allyl compound is:

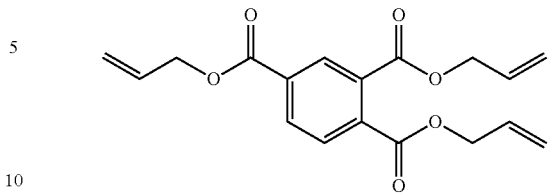

Grafting reactions with initiation of the radical formers according to the invention are implemented in the presence of unsaturated monomers, which are bonded onto the polymer backbone by the reaction by means of a chemical bond. Suitable unsaturated monomers are in particular maleic anhydride, itaconic anhydride, N-alkylmaleimide, acrylic acid, methacrylic acid, acrylic ester, methacrylic ester, such as e.g. lauryl(meth)acrylate, stearyl (meth) acrylate, glycidyl (meth)acrylate, hydroxyethyl(meth)acrylate.

Furthermore, it can be advantageous to implement the crosslinking- or grafting reaction in the presence of an additional nitroxyl radical. By means of the addition of the nitroxyl radical, the crosslinking- or grafting reaction can be moderated, i.e. the reaction course can be controlled better, which leads to fewer secondary reactions of the process. Suitable nitroxyl radicals are for example:

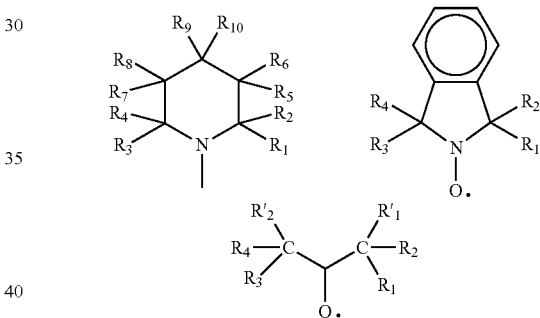

$R_1$-$R_{10}$ representing a possibly substituted alkyl group, phenyl, hydroxyl, alkoxy or ester group and being commercially available for example under the names TEMPO, Hydroxy-TEMPO or Oxo-TEMPO. The following nitroxyl radicals are particularly preferred:

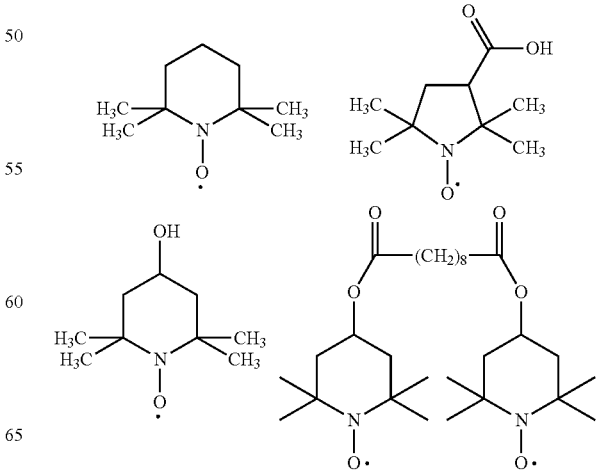

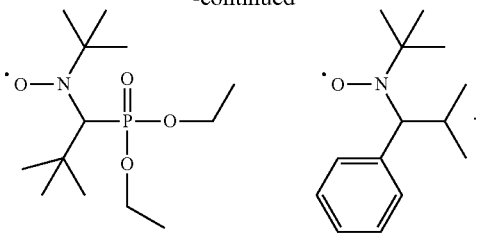

Furthermore, it can be advantageous that the degradation-, crosslinking- or grafting reactions of the oxyimides according to the invention are effected with the further addition of catalytically acting compounds. Such compounds can be for example metal salts of transition metals, such as e.g. copper, manganese or iron, for example in the form of acetates, such as Cu(I)acetate.

Furthermore, it can be advantageous that the radical formers according to the invention are combined with at least one further radical former, e.g. with different classes of radical formers and/or radical formers with different decomposition temperatures. The temperatures at which radicals are formed are chosen such that this formation is effected at the processing temperatures of the respective polymers. The combination of radical formers with different decomposition temperatures is advantageous in the case of multistage processes, thus for example in the case of low temperatures, pre-crosslinking and, in the case of a higher temperature, further crosslinking of polyethylene can be effected.

Radical formers in the sense of the present invention are compounds which can produce radicals by thermal and light-induced cleavage. Suitable radical formers for the applications present here are those which, for the plastic material- or coating processing processes in which degradation, crosslinking or grafting is effected, deliver a sufficient quantity of radicals for the reaction.

The further radical former is thereby preferably selected from the group consisting of peroxides, N-alkoxyamines, —C—C— radical formers, radical formers with azo groups (—N=N—), radical formers with hydrazine groups (—NH—HN—), radical formers with hydrazone groups (>C=N—NH—), radical formers with azine groups (>C=N—N=C<), radical formers with triazene groups (—N=N—N<) and iminoxytriazines.

The production of suitable azo compounds is described for example in M. Aubert et al. Macromol. Sci. Eng. 2007, 292, 707-714 or in WO 2008101845, the production of hydrazones and azines in M. Aubert et al., Pol. Adv. Technol. 2011, 22, 1529-1538, the production of triazenes in W. Pawelec et al., Pol. Degr. Stab. 2012, 97, 948-954. The synthesis of iminoxytriazines is described in WO 2014/064064.

Peroxides are commercially available compounds, which can be obtained for example from United Initiators. Suitable peroxides are for example:

2,5-dimethyl-2,5-di(t-butylperoxy)hexane, 2,5-dimethyl-2,5-di(t-butyl-peroxy)hexyne-3,3,6,6,9,9-pentamethyl-3-(ethylacetate)-1,2,4,5-tetraoxycyclononane, t-butylhydroperoxide, hydrogen peroxide, dicumylperoxide, t-butylperoxyisopropylcarbonate, di-t-butylperoxide, p-chlorobenzoylperoxide, dibenzoyldiperoxide, t-butylcumylperoxide, t-butylhydroxyethylperoxide, di-t-amylperoxide, 2,5-dimethylhexene-2,5-diperisononanoate, acetylcyclohexanesulphonylperoxide, diisopropylperoxydicarbonate, tert-amylperneodecanoate, tert-butyl-perneodecanoate, tert-butylperpivalate, tert-amylperpivalate, bis(2,4-dichlorobenzoyl)peroxide, diisononanoylperoxide, didecanoylperoxide, dioctanoylperoxide, dilauroylperoxide, bis(2-methylbenzoyl)peroxide, disuccinoylperoxide, diacetylperoxide, dibenzoylperoxide, tert-butylper-2-ethylhexanoate, bis(4-chlorobenzoyl)peroxide, tert-butylperisobutyrate, tert-butylpermaleate, 1,1-bis(tert-butylperoxy)-3,5,5-trimethylcyclohexane, 1,1-bis(tert-butylperhydroperoxide.

The at least one further radical former is thereby particularly preferably selected from the group consisting of
a) N-alkoxyamines according to the subsequently illustrated structural formula

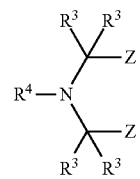

$R^3$ standing for hydrogen or a possibly substituted alkyl-, cycloalkyl-, aryl-, heteroaryl- or acyl-radical, in particular being a C1 to C4 alkyl radical,
$R^4$ standing for an alkoxy-, aryloxy-, cycloalkoxy-, aralkoxy- or acyloxy-radical,
Z standing for hydrogen or a possibly substituted alkyl-, cycloalkyl-, aryl-, heteroaryl- or acyl-radical, the two radicals Z also being able to form a closed ring which can be substituted possibly by ester-, ether-, amine-, amide-, carboxy- or urethane groups,
b) azo compounds according to the subsequently illustrated structural formulae

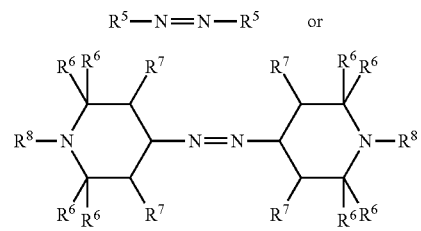

$R^5$ meaning an alkyl-, cycloalkyl- or aryl-radical,
$R^6$ upon each occurrence, being the same or different and meaning a linear or branched alkyl-radical,
$R^7$ upon each occurrence, being the same or different and meaning hydrogen or a linear or branched alkyl-radical, and
$R^8$ upon each occurrence, being the same or different and meaning an alkyl-, alkoxy-, aryloxy-, cycloalkyloxy-, aralkoxy- or acyloxy-radical,
c) dicumyl according to the subsequently illustrated structural formula

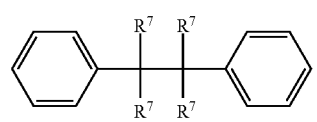

$R^7$ having the previously indicated meaning, preferably being methyl, d) and/or polycumyl according to the subsequently illustrated structural formula

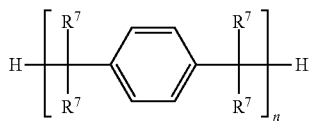

$R^7$ having the previously indicated meaning, preferably being methyl, and 2<n<100.

Typical examples of the previously mentioned N-alkoxyamines of the indicated structure are thereby:

1-cyclohexyloxy-2,2,6,6-tetramethyl-4-octadecylaminopiperidine; bis(1-octyloxy-2,2,6,6-tetramethylpiperidin-4-yl)sebacate; 2,4-bis[(1-cyclohexyloxy-2,2,6,6-tetramethylpiperidin-4-yl)butylamino]-6-(2-hydroxyethylamino-S-triazine; bis(1-cyclohexyloxy-2,2,6,6-tetramethylpiperidin-4-yl)adipate;

2,4-bis[(1-cyclohexyloxy-2,2,6,6-tetramethylpiperidin-4-yl)butylamino]-6-chloro-S-triazine; 1-(2-hydroxy-2-methylpropoxy)-4-hydroxy-2,2,6,6-tetramethylpiperidine; 1-(2-hydroxy-2-methylpropoxy)-4-oxo-2,2,6,6-tetramethylpiperidine; 1-(2-hydroxy-2-methylpropoxy)-4-octadecanoyloxy-2,2,6,6-tetramethylpiperidine; bis(1-(2-hydroxy-2-methylpropoxy)-2,2,6,6-tetramethylpiperidin-4-yl)sebacate; bis(1-(2-hydroxy-2-methylpropoxy)-2,2,6,6-tetramethylpiperidin-4-yl)adipate; 2,4-bis{N-[1-(2-hydroxy-2-methylpropoxy)-2,2,6,6-tetramethylpiperidin-4-yl]-N-butylamino}-6-(2-hydroxyethylamino)-S-triazine);

4-piperidinol, 2,2,6,6-tetramethyl-1-(undecyloxy)-,4,4'-carbonate; the reaction product of 2,4-bis[(1-cyclohexyloxy-2,2,6,6-tetramethylpiperidin-4-yl)butylamino]-6-chloro-S-triazine with N,N'-bis(3-aminopropylethylenediamine); the oligomer compound, which is the condensation product of 4,4'-hexamethylene-bis(amino-2,2,6,6-tetramethylpiperidine) and 2,4-dichloro-6-[(1-cyclohexyloxy-2,2,6,6-tetramethyl-4-yl)butylamino]-S-triazine, closed at the ends with 2-chloro-4,6-bis(dibutylamino)-S-triazine; aliphatic hydroxylamine, such as e.g. distearyl hydroxylamine; and also compounds of the formulae

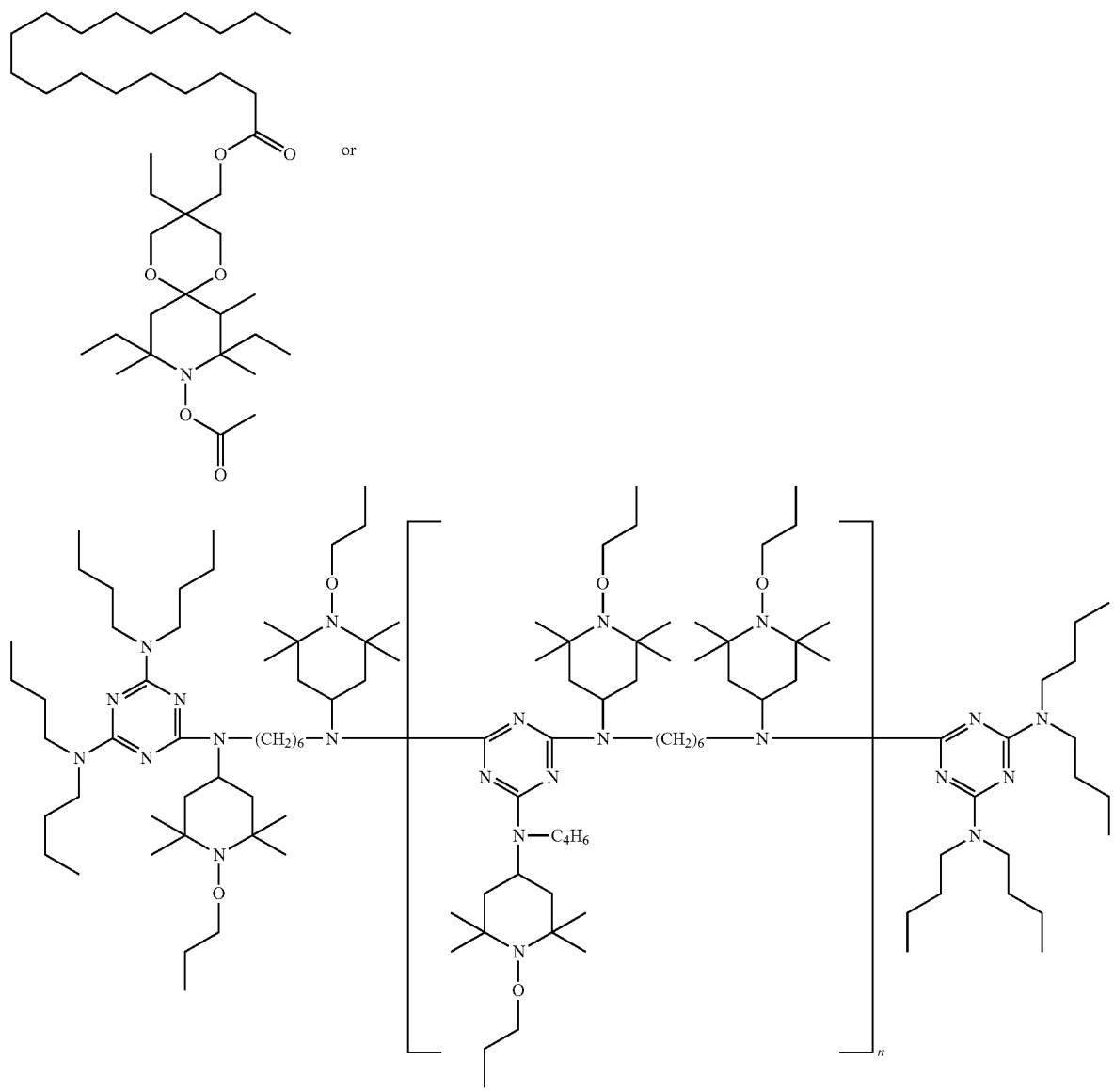

in which n=1–15.

The above-mentioned compounds are partially commercial products and are sold under the following trade names: FLAMESTAB NOR 116®, TINUVIN NOR 371®, IRGATEC CR 76® by BASF SE, Hostavin NOW® by Clariant or ADK Stab LA 81® by Adeka. Dicumyl and polycumyl are commercially available products which are obtainable for example from United Initiators.

The plastic materials can comprise preferably normal additives, e.g. additives selected from the group consisting of UV absorbers, light stabilisers, stabilisers, hydroxylamines, benzofuranones, flame retardants, nucleation agents, impact strength enhancers, plasticisers, lubricants, rheology modifiers, processing aids, pigments, colourants, optical brighteners, antimicrobial active substances, antistatic agents, slip agents, antiblocking agents, coupling means, chain lengtheners, dispersants, compatibilisers, oxygen collectors, acid collectors, marking means or anti-fogging means. In a preferred embodiment, the compositions comprise in particular acid collectors, e.g. based on salts of long-chain acids, such as e.g. calcium stearate, magnesium stearate, zinc stearate, calcium lactate calciumstearoyl-2-lactylate, or of hydrotalcites and/or stabilisers from the group of phenolic antioxidants and phosphites and/or light stabilisers from the group of hindered amines (HALS) and/or dispersants.

Suitable light stabilisers are for example compounds based on 2-(2'-hydroxyphenyl)benzotriazoles, 2-hydroxybenzophenones, esters of benzoic acids, acrylates, oxamides and 2-(2-hydroxyphenyl)-1,3,5-triazines.

Suitable 2-(2"-hydroxyphenyl)benzotriazoles are for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-ylphenol]; the product of reesterification of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$, wherein R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]benzotriazole, 2-[2'-hydroxy-3'-(1,1,3,3-tetramethylbutyl)-5'-(α,α-dimethylbenzyl)phenyl]benzotriazole.

Suitable 2-hydroxybenzophenones are for example 4-hydroxy-, 4-methoxy-, 4-octyloxy-, 4-decyloxy-4-dodecyloxy, 4-benzyloxy, 4,2',4'-trihydroxy- and 2'-hydroxy-4,4'-dimethyoxy derivatives of 2-hydroxybenzophenones.

Suitable acrylates are for example ethyl-α-cyano-β,β-diphenylacrylate, isooctyl-α-cyano-β,β-diphenylacrylate, methyl-α-carbomethoxycinnamate, methyl-α-cyano-β-methyl-p-methoxycinnamate, butyl-α-cyano-β-methyl-p-methoxycinnamate, methyl-α-carbomethoxy-p-methoxycinnamate and N -(β-carbomethoxy-β-cyanovinyl)-2-methylindoline.

Suitable esters of benzoic acids are for example 4-tert-butylphenylsalicylate, phenylsalicylate, octylphenylsalicylate, dibenzoylresorcinol, bis(4-tert-butylbenzoyl)resorcinol, benzoylresorcinol, 2,4-di-tert-butylphenyl-3,5-di-tert-butyl-4-hydroxybenzoate, hexadecyl-3,5-di-tert-butyl-4-hydroxybenzoate, octadecyl-3,5-di-tert-butyl-4-hydroxybenzoate, 2-methyl-4,6-di-tert-butylphenyl-3,5-di-tert-butyl-4-hydroxybenzoate.

Suitable oxamides are for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and the mixtures thereof with 2-ethoxy-2'-ethyl-5,4'-di-tert-butoxanilide, mixtures of o- and p-methoxy-disubstituted oxanilides and mixtures of o- and p-ethoxy-disubstituted oxanilides.

Suitable 2-(2-hydroxyphenyl)-1,3,5-triazines are for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl-1,3,5-triazine.

Suitable metal deactivators are for example N,N'-diphenyloxamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyldihydrazide, oxanilide, isophthaloyldihydrazide, sebacoylbisphenylhydrazide, N,N'-diacetyladipoyldihydrazide, N,N'-bis(salicyloyl)oxylyldihydrazide, N,N'-bis(salicyloyl)thiopropionyldihydrazide.

In particular, the following structures are suitable as metal deactivators:

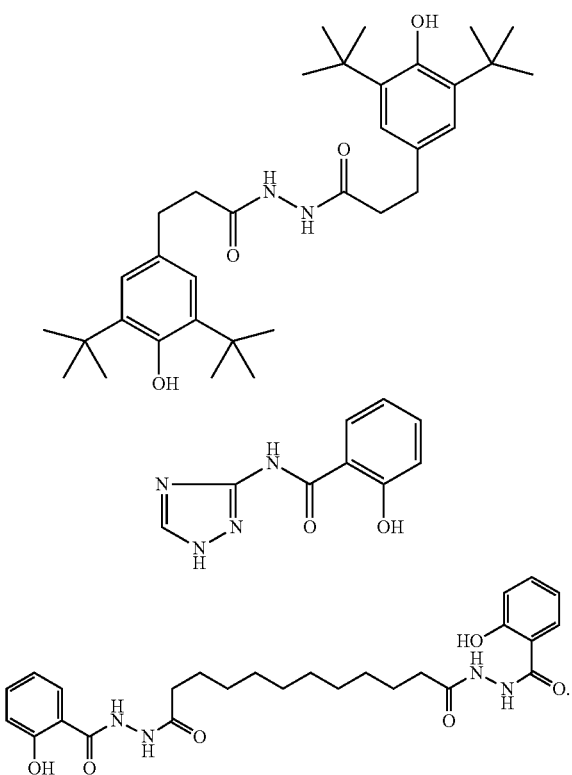

Suitable phenolic antioxidants are for example:

alkylated monophenols, such as e.g. 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, linear or branched nonylphenols, such as e.g. 2,6-dinonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures hereof;

alkylthiomethylphenols, such as e.g. 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol;

hydroquinones and alkylated hydroquinones, such as e.g. 2,6-di-tert-butyl-4-methyoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenylstearate, bis(3,5-di-tert-butyl-4-hydroxylphenyl)adipate;

tocopherols, such as e.g. α-, β-, γ-, δ-tocopherol and mixtures of these (vitamin E);

hydroxylated thiodiphenylethers, such as e.g. 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide;

alkylidene bisphenols, such as e.g. 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol, 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol-bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis-(5-tert-butyl-4-hydroxy-2-methylphenyl)-4-n-dodecylmercaptobutane, 1,1,5,5-tetra(5-tert-butyl-4-hydroxy-2-methylphenyl)pentane;

O-, N- and S-benzyl compounds, such as e.g. 3,5,3',5'-tetra-tert-butyl-4,4'-dihydroxydibenzylether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate;

hydroxybenzylated malonates, such as e.g. dioctadecyl-2,2-bis(3,5-di-tert-butyl-2-hydroxybenzyl)malonate, dioctadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate;

aromatic hydroxybenzyl compounds, such as e.g. 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol;

triazine compounds, such as e.g. 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxphenylethyl)-1,3,5-triazine, 1,3,5-tris(3,5-di-tert-butyl-4-hydroyphenylpropionyl)hexahydro-1,3,5-triazine, 1,3,5-tris(3,5-dicyclohexyl-4-hydroxybenzyl)isocyanurate;

benzylphosphonates, such as e.g. dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethylester of 3,5-di-tert-butyl-4-hydroxybenzylphosphonic acid;

acylaminophenols, such as e.g. 4-hydroxylauranilide, 4-hydroxystearanilide, octyl-N-(3,5-di-tert-butyl-4-hydroxyphenyl)carbamate;

esters of β-(3,5-di-tert-butyl-4-hydroxyphenyl)propionic acid with mono- or multivalent alcohols, e.g. methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, esters of β-(5-tert-butyl-4-hydroxy-3-methylphenyl)propionic acid with mono- or multivalent alcohols, e.g. methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, 3,9-bis[2-{3-(3-tert-butyl-4-hydroxy-5-methylphenyl)propionyloxy}-1,1-dimethylethyl]-2,4,8,10-tetraoxaspiro[5.5]undecane;

esters of β-(3,5-dicyclohexyl-4-hydroxyphenyl)propionic acid with mono- or multivalent alcohols, e.g. methanol, ethanol, octanol, octadecaneol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane;

esters of 3,5-di-tert-butyl-4-hydroxyphenyl)acetic acid with mono- or multivalent alcohols, e.g. methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane;

amides of β-(3,5-di-tert-butyl-4-hydroxyphenyl)propionic acid, such as e.g. N,N'-bis(3,5-di-tert-butyl-4-hydroxyphenylpropionyl)hexamethylenediamide, N,N'-bis(3,5-di-tert-butyl-4-hydroxyphenylpropionyl) hexamethylenediamide, N,N'-bis(3,5-di-tert-butyl-4-hydroxyphenylpropionyl)hexamethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1, marketed by Uniroyal);

ascorbic acid (vitamin C).

Particularly preferred phenolic antioxidants are:
octadecyl-3-(3,5-di-tert-butyl-4-hydroxyphenyl)propionate, pentaerythritol-tetrakis[3-(3,5-di-tert-butyl-4-hydroxyphenyl)propionate, tris(3,5-di-tert-butyl-4-hydroxyphenyl)isocyanurate, 1,3,5-trimethyl-2,4,6-tris(3,5-di-tert-butyl-4-hydroxyphenyl)isocyanurate, 1,3,5-trimethyl-2,4,6-tris(3,5-di-tert-butyl-4-hydroxybenzyl)benzene, triethylene glycol-bis[3-(3-tert-butyl-4-hydroxy-5-methylphenyl)propionate, N,N'-hexan-1,6-diyl-bis[3-(3,5-di-tert-butyl-4-hydroxyphenyl)propionic acid amide.

Suitable phosphites/phosphonites are for example:
triphenylphosphite, diphenylalkylphosphites, phenyldialkylphosphites, tri(nonylphenyl)phosphite, trilaurylphosphites, trioctadecylphosphite, distearylpentaerythritoldiphosphite, tris-(2,4-di-tert-butylphenyl)phosphite, diisodecylpentaerythritoldiphosphite, bis(2,4-di-tert-butylphenyl)pentaerythritoldiphosphite, bis(2,4-di-cumylphenyl)pentaerythritoldiphosphite, bis(2,6-di-tert-butyl-4-methylphenyl)pentaerythritoldiphosphite, diisodecyloxypentaerythritoldiphosphite, bis(2,4-di-tert-butyl-6-methylphenyl)pentaerythritoldiphosphite, bis(2,4,6-tris(tert-butylphenyl)pentaerythritoldiphosphite, tristearylsorbitoltriphosphite, tetrakis(2,4-di-tert-butylphenyl)-4,4'-biphenylenediphosphonite, 6-isooctyloxy-2,4,8, 10-tetra-tert-butyl-12H-dibenzo[d,g]-1,3,2-dioxaphosphocine, bis(2,4-di-tert-butyl-6-methylphenyl)methylphosphite, bis(2,4-di-tert-butyl-6-methylphenyl)ethylphosphite, 6-fluoro-2,4,8, 10-tetra-tert-butyl-12-methyldibenzo[d,g]-1,3,2-dioxaphosphocine, 2,2'2"-nitrilo[triethyltris(3,3",5,5'-tetra-tert-butyl-1,1'-biphenyl-2,2'-diyl)phosphite], 2-ethylhexyl (3,3',5,5'-tetra-tert-butyl-1,1'-biphenyl-2,2'-diyl))phosphite, 5-butyl-5-ethyl-2-(2,4,6-tri-tert-butylphenoxy)-1,3,2-dioxaphosphirane.

Particularly preferred phosphites/phosphonites are:

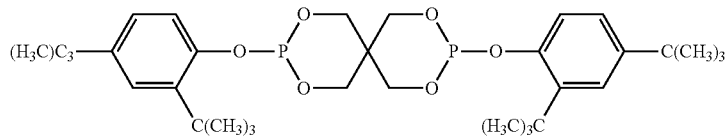

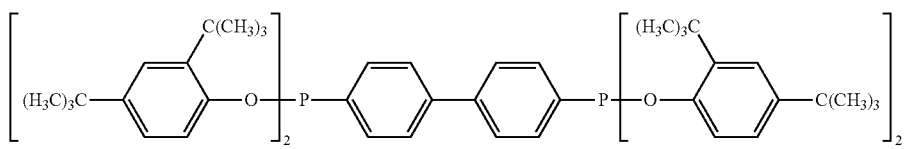

-continued

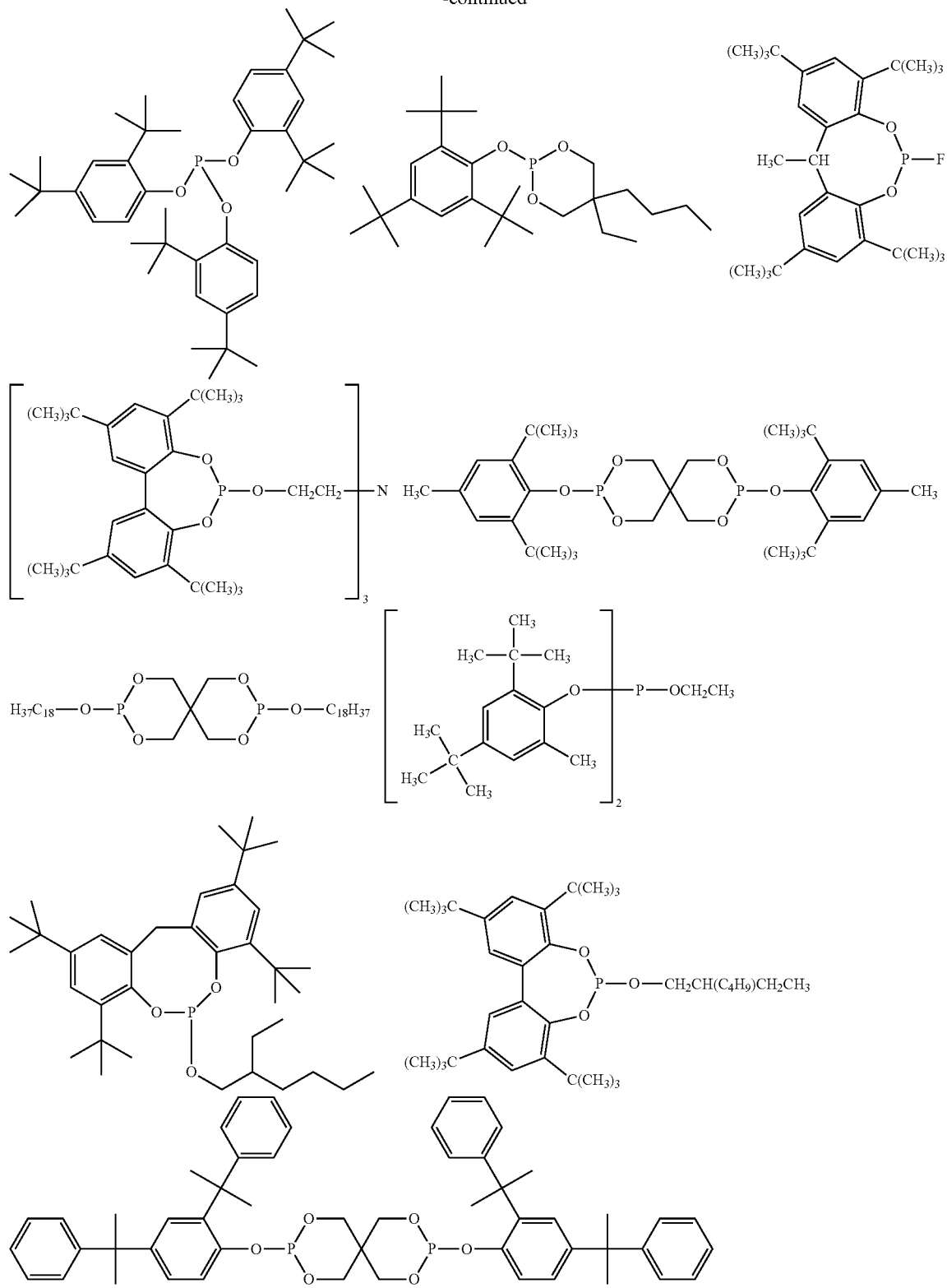

Further suitable stabilisers are aminic antioxidants. Suitable aminic antioxidants are for example:

N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulphamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, e.g. p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene and also mixtures or combinations hereof.

Further suitable aminic antioxidants are hydroxylamine, or N-oxides (nitrons), such as e.g. N,N-dialkylhydroxylamines, N,N-dibenzylhydroxylamine, N,N-dilaurylhydroxylamine, N,N-distearylhydroxylamine, N-benzyl-α-phenylnitron, N-octadecyl-α-hexadecylnitron, and also Genox EP (Addivant) according to the formula:

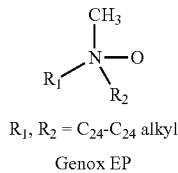

$R_1, R_2 = C_{24}-C_{24}$ alkyl

Genox EP

Further suitable stabilisers are thiosynergists. Suitable thiosynergists are, for example, distearylthiodipropionate, dilauryldipropionate or the compound according to the following formula:

Further suitable stabilisers, in particular for polyamides, are copper salts, such as e.g. copper(I)iodide, copper(I) bromide or copper complexes, such as e.g. triphenylphosphine-copper(I) complexes.

Suitable hindered amines are for example 1,1-bis(2,2,6,6-tetramethyl-4-piperidyl) succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)-n-butyl-3,5-di-tert-butyl-4-hydroxybenzylmalonate, the condensation product of 1-(2-hydroxyethyl)-2,2,6,6-tetramethyl-4-hydroxypiperidine und succinic acid, linear or cyclic condensation products of N,N'-bis(2,2,6,6-tetramethyl-4-piperidyl)hexamethylenediamine and 4-tert-octylamino-2,6-di-chloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethandiyl)-bis(3,3,5,5-tetramethylpiperazinone), 4-benzoyl-2,2,6,6-tetramethylpiperidine, 4-stearyloxy-2,2,6,6-tetramethylpiperidine, linear or cyclic condensation products of N,N'-bis(2,2,6,6-tetramethyl-4-piperidyl)hexamethylenediamine and 4-morpholino-2,6-dichloro-1,3,5-triazine, the reaction product of 7,7,9,9-tetramethyl-2-cycloundecyl-1-oxa-3,8-diaza-4-oxospiro-[4,5]decane and epichlorhydrin.

Suitable flame retardants are for example:
a) inorganic flame retardants, such as e.g. $Al(OH)_3$, $Mg(OH)_2$, $AlO(OH)$, $MgCO_3$, layer silicates, such as e.g. montmorillonite or sepiolite, non- or organically modified double salts, such as e.g. Mg—Al-silicates, POSS-(Polyhedral Oligomeric Silsesquioxane) compounds, huntite, hydromagnesite or halloysite and also $Sb_2O_3$, $Sb_2O_5$, $MoO_3$, zinc stannate, zinc hydroxystannate,
b) nitrogen-containing flame retardants, such as e.g. melamine, melem, melam, melon, melamine derivatives, melamine condensation products or melamine salts, benzoguanamine, polyisocyanurates, allantoin, (poly)phosphacenes, in particular melamine cyanurate, melamine phosphate, dimelamine phosphate, melamine pyrophosphate, melamine polyphosphate, melamine-methane phosphonate, melamine-metal phosphates, such as e.g. melamine aluminium phosphate, melamine zinc phosphate, melamine magnesium phosphate, and also the corresponding pyrophosphates and polyphosphates, ethylene diamine-methane phosphonate, poly-[2,4-(piperazin-1,4-yl)-6-(morpholin-4-yl)-1,3,5-triazine], ammonium polyphosphate, melamine borate, melamine hydrobromide,

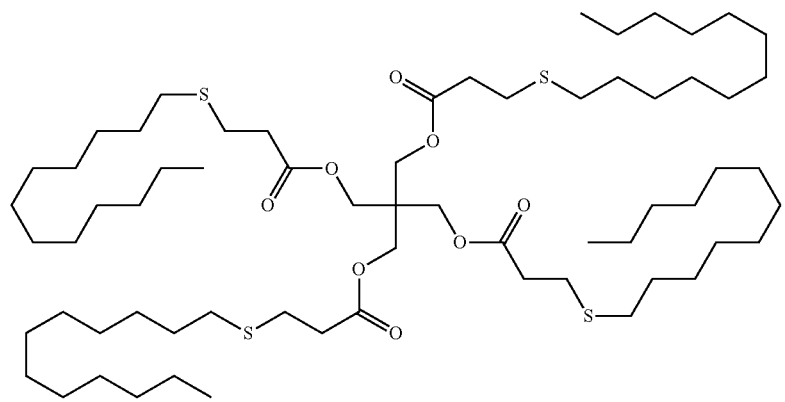 [SMILES: CCCCCCCCCCCCSCCC(=O)OCC(COC(=O)CCSCCCCCCCCCCCC)(COC(=O)CCSCCCCCCCCCCCC)COC(=O)CCSCCCCCCCCCCCC]

c) phosphorus-containing flame retardants, such as e.g. inorganic or organic phosphonates, such as e.g. aluminium phosphonate, phosphonate ester, oligomeric and polymeric derivatives of methane phosphonic acid, red phosphorus, phosphates, such as e.g. resorcin diphosphate, bisphenol-A-diphosphate and the oligomers thereof, triphenylphosphate, ethylene diamine diphosphate, phosphinates, such as e.g. salts of hypophosphorous acid and the derivatives thereof, such as alkyl phosphinate salts e.g. diethylphosphinate aluminium or diethylphosphinate zinc or aluminium phosphinate, aluminium phosphite, aluminium phosphate, 9,10-dihydro-9-oxa-10-phosphorylphenanthrene-10-oxide (DOPO) and the substituted compounds thereof, d) halogen-containing flame retardants based on chlorine and bromine, such as e.g polybrominated diphenyl oxides, such as e.g. decabromodiphenyl oxide, tris(3-bromo-2,2-bis(bromomethyl)propyl phosphate, tris(tribromoneopentyl)phosphate, tetrabromophthalic acid, 1,2-bis(tribromophenoxy)ethane, hexabromocyclododecane, brominated diphenylethane, tris-(2,3-dibromopropyl)isocyanurate, ethylene-bis(tetrabromophthalimide), tetrabromobisphenol A, brominated polystyrene, brominated polybutadiene or polystyrene-brominated polybutadiene copolymers, brominated epoxy resin, polypentabromobenzyl acrylate, possibly in combination with $Sb_2O_3$ and/or $Sb_2O_5$, e) borates, such as e.g. zinc borate or calcium borate, possibly on carrier materials such as silica, f) sulphur-containing compounds such as e.g. elementary sulphur, disulfides, and polysulfides, thiuram sulfide, dithiocarbamates, mercaptobenzathiozol and sulphenamides, g) antidrip agents, such as e.g. polytetrafluorethylene, h) silicon-containing compounds, such as e.g. polyphenylsiloxanes, i) carbon modifications such as e.g. carbon nanotubes (CNT) or graphene and also combinations or mixtures hereof.

Suitable dispersants are for example:

polyacrylates, e.g. copolymers with long-chain side groups, polyacrylate-block copolymers, alkylamides: e.g. N,N'-1,2-ethanediylbisoctadecanamide sorbitan ester, e.g. monostearylsorbitan ester, titanates and zirconates, reactive copolymers with functional groups e.g. polypropylene-co-acrylic acid, polypropylene-co-maleic anhydride, polyethylene-co-glycidylmethacrylate, polystyrene-alt-maleic anhydride-polysiloxanes: e.g. dimethylsilanediolethylene oxide copolymer, polyphenylsiloxane copolymer, amphiphilic copolymers: e.g. polyethylene-block-polyethylene oxide, dendrimers, e.g. hydroxyl group-containing dendrimers.

Suitable nucleation agents are for example talc, alkali or alkaline earth salts of mono- and polyfunctional carboxylic acids, such as e.g. benzoic acid, succinic acid, adipic acid, e.g. sodium benzoate, zinc glycerolate, aluminium hydroxy-bis(4-tert-butyl)benzoate, benzylidene sorbitols, such as e.g. 1,3:2,4-bis(benzylidene)sorbitol or 1,3:2,4-bis(4-methyl-benzylidene)sorbitol, 2,2"-methylene-bis-(4,6-di-tert-butyl-phenyl)phosphate, and also trisamides, such as e.g. according to the following structures

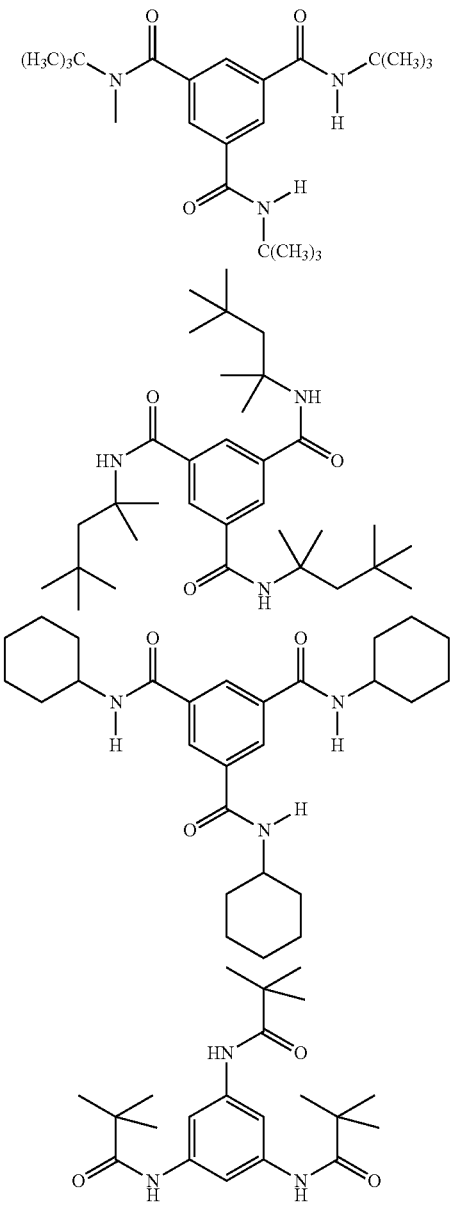

Suitable fillers and reinforcing materials are for example synthetic or natural materials, such as e.g. calcium carbonate, silicates, glass fibres, glass balls (solid or hollow), talc, mica, kaolin, barium sulfate, metal oxides and metal hydroxides, carbon black, graphite, carbon nanotubes, graphene, sawdust or fibres of natural products, such as e.g. cellulose, synthetic fibres or metal fibres. Further suitable fillers are hydrotalcites or zeolites or layer silicates, such as e.g. montmorillonite, bentonite, beidellite, mica, hectorite, saponite, vermiculite, ledikite, magadiite, illite, kaolinite, wollastonite, attapulgite.

Suitable chain-lengtheners for the linear molecular weight increase of polycondensation polymers, such as polyesters or polyamides are for example diepoxides, bis-oxazolines, bis-oxazolones, bis-oxazines, diisocyanates, dianhydrides, bis-acyllactams, bis-maleimides, dicyanates, carbodiimides. Further suitable chain-lengtheners are polymeric compounds, such as e.g. polystyrene-polyacrylate-polyglycidyl (meth)acrylate copolymers, polystyrene-maleic anhydride copolymers and polyethylene-maleic anhydride copolymers.

Suitable pigments can be of an inorganic or organic nature. Suitable inorganic pigments are for example titanium dioxide, zinc oxide, zinc sulfide, iron oxide, ultramarine, carbon black. Suitable organic pigments are for example anthraquinones, anthanthrones, benzimidazolones, quinacridones, diketopyrrolopyrroles, dioxazines, indanthrones, isoindolinones, azo compounds, perylenes, phthalocyanines or pyranthrones. Further suitable pigments are effect pigments based on metal or pearlescent pigments based on metal oxide.

Optical brighteners are for example bisbenzoxazoles, phenylcoumarins or bis(styryl)biphenyls and in particular optical brighteners of the formulae:

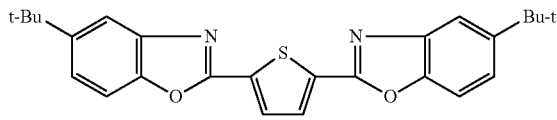

Suitable filler deactivators are for example glycidyl-based epoxides, such as e.g. bis-phenol-A-diglycidylethers, or bisphenol-F-diglycidylethers, and the oligomers thereof or polymer resins, polysiloxanes, polyacrylates, in particular block copolymers, such as polymethacrylic acid-polyalkylene oxide or polystyrene-polyacrylate-polyglycidy(meth)acrylate copolymers.

Suitable antistatic agents are for example ethoxylated alkylamines, fatty acid esters, akylsulphonates and polymers, such as e.g. polyether amides or copolymers, which comprise salts of acrylic acid, such as e.g. polyethylene-polyacrylate-polyacrylate-Na copolymers.

According to the present invention, the previously illustrated organic oxyimides can be used for modification (degradation, crosslinking, grafting) of the following plastic materials:

a) polymers made of olefins or diolefins, such as e.g. polyethylene (LDPE, LLDPE, VLDPE, ULDPE, MDPE, HDPE, UHMWPE), metallocene-PE (m-PE), polypropylene, polyisobutylene, poly-4-methylpentene-1, polybutadiene, polyisoprene, polycyclooctene, polyalkylene-carbon monoxide copolymers, and also copolymers in the form of statistical or block structures, such as e.g. polypropylene-polyethylene (EP), EPM or EPDM, ethylene-vinyl acetate (EVA), ethylene-acrylic ester, such as e.g. ethylene-butyl acrylate, ethylene-acrylic acid and the salts thereof (ionomers), and also terpolymers, such as e.g. ethylene-acrylic acid-glycidylacrylate, graft polymers, such as e.g. polypropylene-graft-maleic anhydride, polypropylene-graft-acrylic acid, polyethylene-graft-acrylic acid, polyethylene-polybutacrylate-graft-maleic anhydride, b) polystyrene, polymethylstyrene, polyvinyl naphthalene, styrene-butadiene (SB), styrene-butadiene-styrene (SBS), styrene-ethylene-butylene-styrene (SEBS), styrene-ethylene-propylene-styrene, styrene-isoprene, styrene-isoprene-styrene (SIS), styrene-butadiene-acrylonitrile (ABS), styrene-acrylonitrile-acrylate (ASA), styrene-ethylene, styrene-maleic anhydride polymers incl. corresponding graft copolymers, such as e.g. styrene on butadiene, maleic anhydride on SBS or SEBS, and also graft copolymers made of methylmethacrylate, styrene-butadiene and ABS (MABS), c) halogen-containing polymers, such as e.g polyvinyl chloride (PVC), polychloroprene and polyvinylidene chloride (PVDC), copolymers made of vinyl chloride and vinylidene chloride or made of vinyl chloride and vinyl acetate, chlorinated polyethylene, polyvinylidene fluoride, d) polymers of unsaturated esters, such as e.g polyacrylates and polymethacrylates, such as polymethylmethacrylate (PMMA), polybutylacrylate, polylaurylacrylate, polystearylacrylate, polyglycidylacrylate, polyglycidylmethacrylate, polyacrylonitrile, polyacrylamides, copolymers, such as e.g. polyacrylonitrile-polyalkylacrylate, polymethacrylimide, e) polymers made of unsaturated alcohols and derivates, such as e.g. polyvinyl alcohol, polyvinyl acetate, polyvinyl butyral, f) polyacetals, such as e.g. polyoxymethylene (POM) or copolymers with e.g. butanal, g) polyphenylene oxides and blends with polystyrene or polyamides, h) polymers of cyclic ethers, such as e.g. polyethylene glycol, polypropylene glycol, polyethylene oxide, polypropylene oxide, i) polyurethanes made of hydroxy-terminated polyethers or polyesters and aromatic or aliphatic isocyanates, in particular linear polyurethanes, polyureas, j) polyamides, such as e.g. polyamide 6, 6.6, 6.10, 4.6, 4.10, 6.12, 12.12, polyamide 11, polyamide 12 and also (partially) aromatic polyamides, such as e.g. polyphthalamides, e.g. produced from terephthalic acid and/or isophthalic acid and aliphatic diamines or from aliphatic dicarboxylic acids, such as e.g. adipic acid or sebacic acid and aromatic diamines, such as e.g. 1,4- or 1,3-diaminobenzene, blends of different polyamides, such as e.g. PA-6 and PA 6.6 or blends of polyamides and polyolefins, such as e.g. PA/PP, k) polyimides, polyamide imides, polyether imides, polyester imides, poly(ether)ketones, polysulphones, polyethersulphones, polyarylsulphones, polyphenylene sulphide, polybenzimidazoles, polyhydantoins, l) polyesters made of aliphatic or aromatic dicarboxylic acids and diols or made of hydroxycarboxylic acids, such as e.g. polyethylene terephthalate (PET), polybutylene terephthalate (PBT), polypropylene terephthalate, polyethylene naphthalate, poly-1,4-dimethylolcyclohexane terephthalate, polyhydroxybenzoate, polyhydroxynaphthalate, polylactic acid (PLA), polyhydroxybutyrate (PHB), polyhydroxyvalerate (PHV), m) polycarbonates, polyester carbonates, and also blends, such as e.g. PC/ABS, PC/PBT, PC/PET/PBT, PC/PA, n) cellulose derivatives, such as e.g. cellulose nitrate, cellulose acetate, cellulose propionate, cellulose butyrate, o) and also mixtures, combinations or blends made of two or more of the previously mentioned polymers.

Provided that the polymers indicated under a) to n) concern copolymers, these can be present in the form of statistical ("random"), block- or "tapered" structures.

Provided that the polymers indicated under a) to n) concern stereo-regular polymers, these can be present in the form of isotactic, stereotactic, but also in atactic forms or in stereoblock structures.

Furthermore, the polymers indicated under a) to o) can have both amorphous and (partially) crystalline morphologies.

The mentioned polymers a) to n) can thereby not only be present as virgin material, but also in the form of recyclates, e.g. as production waste or as post-consumer recyclates.

According to the invention, the oxyimides of the initially mentioned formula I can be used in the following duromeric or elastomeric, non-thermoplastic plastic materials as radical generators:

a) epoxy resins, consisting of di- or polyfunctional epoxy compounds in combination with e.g. hardeners based on amines, anhydrides, dicyanodiamide, mercaptans, isocyanates or catalytically-acting hardeners, b) phenol resins, such as e.g. phenol-formaldehyde resins, urea-formaldehyde resins, melamine-formaldehyde resins, c) unsaturated polyester resins made of unsaturated dicarboxlic acids and diols, d) silicones, e) polyurethanes as reaction products made of di- or polyfunctional isocyanates and polyols, polyureas, f) alkyd resins, allyl resins.

For very particular preference, the radical generators according to the invention are used for modification in the case of polyolefins, preferably polypropylene and/or polyethylene and the copolymers and blends thereof and also for unsaturated polyester resins.

For very particular preference, the radical generators according to the invention are used preferably for the molecular weight reduction of polypropylene and/or for the crosslinking of polyethylene or unsaturated polyester resins and the copolymers and blends thereof and also for the grafting of unsaturated monomers on polypropylene or polyethylene. For the crosslinking reaction, the hydroxyimides and the hydroxyimide ethers are particularly preferred.

In particular in the case of combinations of the oxyimide used according to the invention with at least one additional radical former, synergistic effects are produced. The additional radical former is thereby preferably selected from the group consisting of the radical formers which are described further back and preferably to be used. In order to avoid repetitions, reference is made to the previous embodiments with respect to the additional radical formers.

In the case of a combined use of the oxyimide used according to the invention with at least one further radical former, it is preferred in the case of the present invention if the previously mentioned compounds are used in a weight ratio (oxyimide: further radical formers) of 99:1 to 1:99, preferably of 5:95 to 95:5, particularly preferably of 10:90 to 90:10.

Furthermore, it is advantageous in the invention if the organic oxyimides, relative to the plastic materials, are used at 0.01 to 30% by weight, preferably at 0.1 to 10% by weight, particularly preferably at 0.5 to 5% by weight.

In addition, the present invention relates to a method for generating radicals in plastic materials, in which at least one organic oxyimide, comprising at least one structural element of the previously described formula I is mixed with a plastic material or with at least one moulding compound comprising at least one plastic material and activated. During activation, radicals are thereby released. In particular, the activation is effected thermally or by irradiation. Particularly preferably, the activation is undertaken simultaneously during a shaping method of the plastic material or of the moulding compound comprising the plastic material, in particular by injection moulding or extrusion. In these methods, the plastic materials are heated above their plasticising temperature from which the plastic material or the moulding compound comprising the plastic material is present in the plasticised state.

The invention relates in addition to the use of the previously mentioned method for modification of the plastic materials.

Particularly preferably, the oxyimides according to the present invention are used as radical generators for controlled degradation of the polymers, in particular polyolefins, in particular polypropylene or for crosslinking of the polymers, in particular polyolefins or unsaturated polyesters, as radical formers for grafting of unsaturated compounds onto the polymers, in particular polyolefins.

With respect to the specific details of the organic oxyimides, which can be used in the method according to the invention or in the purposes of use of the method, reference is made to the previously given embodiments. All of the above-described, preferred embodiments likewise apply, without restriction, also for the above-described method according to the invention or the use according to the invention of the method according to the invention.

The present invention is described in more detail with reference to the subsequent embodiments, without restricting the invention to the examples.

EXAMPLE 1

Molecular Weight Decrease of Polypropylene

The extrusions of the polypropylene samples (Moplen HP 500N) with addition of the radical generators are effected at the indicated temperature and with a screw speed of rotation of 400 rpm on an 11 mm twin-screw extruder (Process 11 of Thermo Scientific). The desired ratio of polymer and additives is firstly homogenised by mixing and supplied for extrusion via volumetric metering. The MVR (melt volume rate) of the granulated extruded samples was determined subsequently at 230° C./2.16 kg according to ISO 1133 and the average weight of the molecular weight was determined by means of high-temperature gel permeation chromatography.

TABLE 1

Compositions in polypropylene and results of the analyses of the melt volume flow rates and of the molecular weight

| Test number | Additive | Extrusion temperature [°] | MVR | Mw |
|---|---|---|---|---|
| Comparative example 1 | Without | 240 | 14 | 400,000 |
| Comparative example 2 | Without | 260 | 15 | 381,000 |
| Comparative example 3 | Without | 280 | 22 | 362,000 |
| Comparative example 4 | Without | 300 | 25 | n.d. |
| Example 1 according to the invention | 0.1% oxyimide 1 | 280 | 45 | n.d. |
| Example 2 | 0.2% oxyimide 1 | 280 | 61 | 244,000 |
| Example 3 | 0.5% oxyimide 1 | 280 | 84 | n.d. |
| Example 4 | 0.2% oxyimide 1 | 240 | 25 | 346,000 |

TABLE 1-continued

Compositions in polypropylene and results of the analyses of the melt volume flow rates and of the molecular weight

| Test number | Additive | Extrusion temperature [°] | MVR | Mw |
|---|---|---|---|---|
| Example 5 | 0.2% oxyimide 1 | 260 | 30 | 317,000 |
| Example 6 | 0.2% oxyimide 1 | 300 | >200 | n.d. |
| Example 7 | 0.1% oxyimide 2 | 280 | 27 | n.d. | n.d. = not determined

Oxyimide 1=N-hydroxyphthalimide

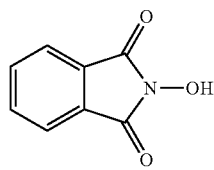 [SMILES: O=C1c2ccccc2C(=O)N1O]

Oxyimide 2 (produced according to WO 2014154636)

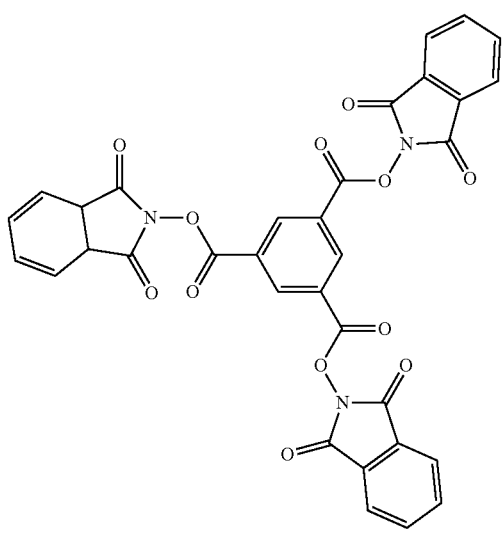 [SMILES: O=C(ON1C(=O)c2ccccc2C1=O)c1cc(C(=O)ON2C(=O)c3ccccc3C2=O)cc(C(=O)ON2C(=O)C3C=CC=CC3C2=O)c1]

Surprisingly, it is shown that the compositions with the oxyimides according to the invention have a higher MVR (=lower molecular weight) and, likewise, in the GPC measurement, a lower molecular weight than the comparative examples. With increasing concentration of oxyimide and increasing processing temperature, the molecular weight reduces furthermore.

EXAMPLE 2

Molecular Weight Increase of Polyethylene

The molecular weight increase of the PE types (obtainable at ExxonMobil) via reactive extrusion with N-hydroxyphthalimide (NHPI) was effected at 200° C., with a screw speed of rotation of 300 rpm on an 11 mm twin-screw extruder (Process 11 of Thermo Scientific). The analyses of the melt volume flow rates (MVR) were effected according to ISO 1133 at a temperature of 190° C. and a weight of 5 kg or 10 kg.

TABLE 2

Compositions in polyethylene and results of the analyses of the melt volume flow rates

| Example | Composition | | MVR (5 kg, 190° C.)/ cm$^3$ * min$^{-1}$ | MVR (10 kg, 190° C.)/ cm$^3$ * min$^{-1}$ |
|---|---|---|---|---|
| Comparative example 1 | LDPE (LD 185 BW) | 100% | 10.2 | 31.7 |
| | NHPI | 0% | | |
| Example 1 according to the invention | LDPE (LD 185 BW) | 99.80% | 9.9 | — |
| | NHPI | 0.20% | | |
| Example 2 according to the invention | LDPE (LD 185 BW) | 99.60% | 9.7 | — |
| | NHPI | 0.40% | | |
| Example 3 according to the invention | LDPE (LD 185 BW) | 99.20% | 9.0 | 31.2 |
| | NHPI | 0.80% | | |
| Comparative example 2 | HDPE (HTA 108) | 100% | — | 12.9 |
| | NHPI | 0% | | |
| Example 4 according to the invention | HDPE (HTA 108) | 99.20% | — | 12.5 |
| | NHPI | 0.80% | | |

With reference to the significant reduction in MVR values of the examples according to the invention relative to the comparative examples, an increase in melt viscosity is shown, which can be attributed to an increase in the molecular weight. Hence, a controlled increase in the molecular weight by means of the method described within the present application can be established.

The invention claimed is:

1. A method of incorporating a radical generator into a plastic material comprising incorporating into said plastic material an organic oxyimide having the structural element of formula I

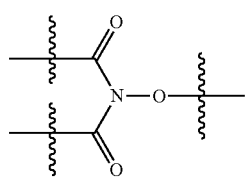

Formula I wherein the radical generator is activated thermally or by irradiation,
wherein the activation is accomplished during shaping of the plastic material or shaping of a moulding compound comprising the plastic material,
wherein the thermal activation is accomplished at a temperature of 240° C. or more,
said method resulting in a modification of the plastic material, wherein the modification is increasing the molecular weight of the plastic material, branching or crosslinking of the plastic material, molecular weight decrease of the plastic material, influencing a molecular weight distribution of the plastic material, and/or grafting of an unsaturated monomer onto the plastic material.

2. The method according to claim 1, wherein the oxyimide is selected from the group consisting of
a) oxyimides comprising at least one structural element of formula II

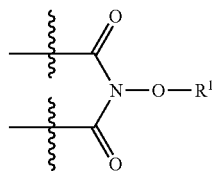

Formula II wherein $R^1$ is hydrogen or an optionally substituted alkyl-, cycloalkyl-, aryl-, heteroaryl- or acyl-radical, and
b) bridged oxyimides comprising at least one structural element of formula III,

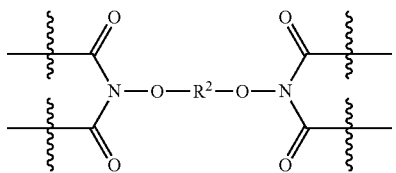

Formula III wherein $R^2$ is an optionally substituted akylene-, cycloalkylene-, arylene-, heteroarylene- or bridging acyl-radical.

3. The method according to claim 2, wherein $R^2$ is selected from the group consisting of
—(CH$_2$)$_n$— with n=1 to 18, —CH(CH$_3$)—, —C(CH$_3$)$_2$—, —O—, —S—, —SO$_2$—, —NHCO—, —CO—

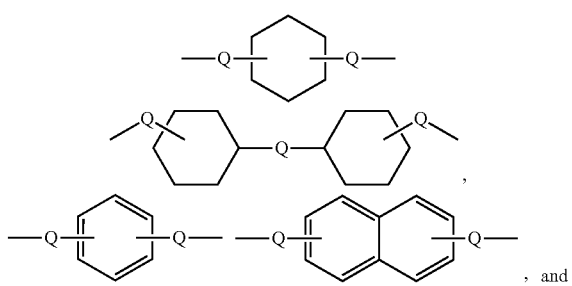

, and

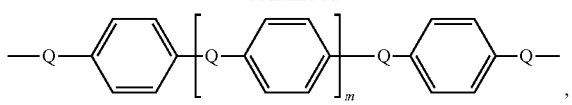

wherein the cycloaliphatic or aromatic ring systems contained in the above groups is unsubstituted or substituted by one or more alkyl- and/or alkoxy-groups, Q upon each occurrence, is the same or different and is selected from the group consisting of a chemical bond, —(CH$_2$)$_n$— with n=1 to 18, —CH(CH$_3$)—, —C(CH$_3$)$_2$—, —O—, —S—, —SO$_2$—, —NHCO—, —CO—, OC(O)—O— and m is 0 or 1 to 18.

4. The method according to claim 1, wherein the organic oxyimide has one of the following formulae,

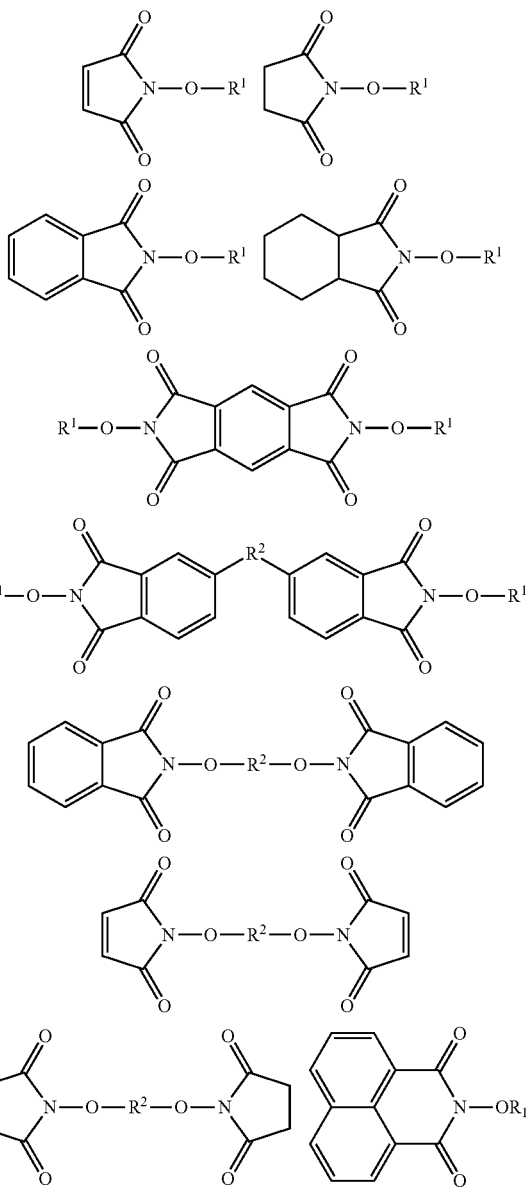

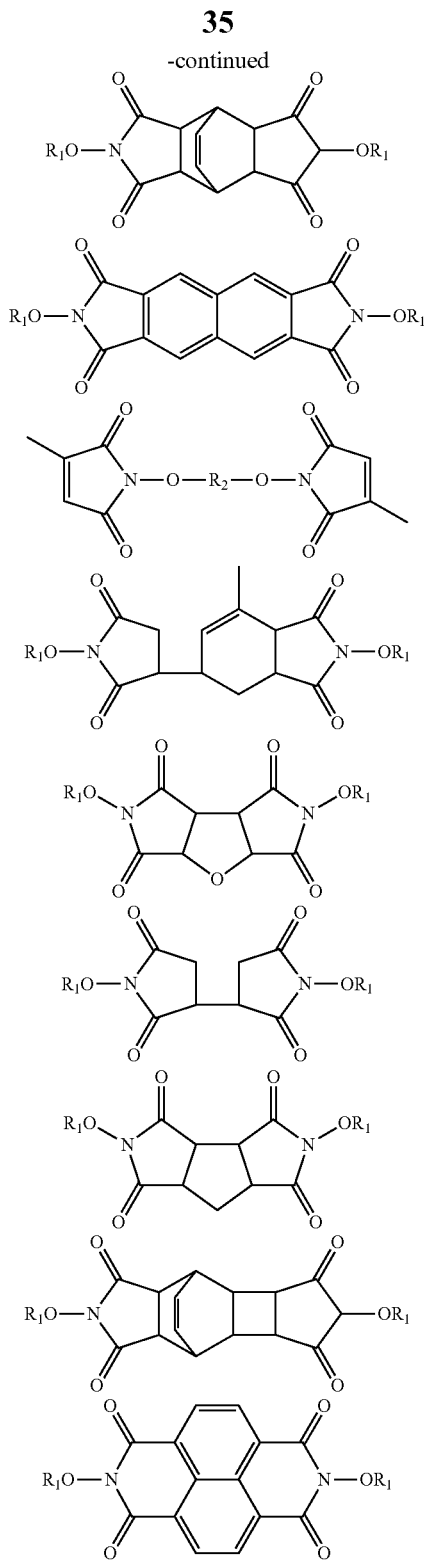

wherein $R^1$ is hydrogen or an optionally substituted alkyl-, cycloalkyl-, aryl-, heteroaryl- or acyl-radical, and $R^2$ is selected from the group consisting of —$(CH_2)_n$— with n=1 to 18, —$CH(CH_3)$—, —$C(CH_3)_2$—, —O—, —S—, —$SO_2$—, —NHCO—, —CO—,

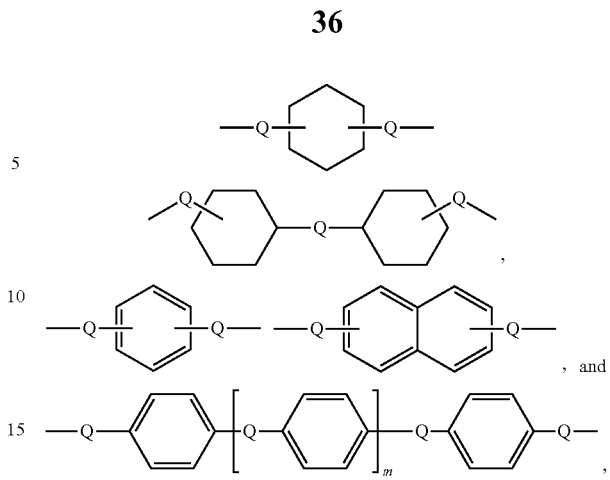

wherein the cycloaliphatic or aromatic ring systems contained in the above groups is unsubstituted or substituted by one or more alkyl- and/or alkoxy-groups, Q upon each occurrence, is the same or different and is selected from the group consisting of a chemical bond, —$(CH_2)_n$— with n=1 to 18, —$CH(CH_3)$—, —$C(CH_3)_2$, —O—, —S—, —$SO_2$—, —NHCO—, —CO—, OC(O)—O— and m is 0 or 1 to 18.

5. The method according to claim 2, wherein $R^1$=H, $R^1$=alkyl or $R^1$=acyl.

6. The method according to claim 1, which further includes incorporating at least one chain transfer agent.

7. The method according to claim 1, which further includes incorporating at least one multifunctional compound selected from the group consisting of a) repeatedly unsaturated oligomers and polymers based on polybutadiene or polyisoprene, b) di- and polyvinyl compounds, c) di- and polyallyl compounds, d) di- and polymaleimides, e) di- and poly(meth)acrylesters of di- and polyalcohols, and f) organofunctional silanes, and combinations thereof.

8. The method according to claim 1, which further includes incorporating at least one nitroxyl radical.

9. The method according to claim 1, which further includes incorporating at least one catalytic compound.

10. The method according to claim 1, which includes incorporating at least one further radical former.

11. The method according to claim 10, wherein the further radical former is selected from the group consisting of N-alkoxyamines, —C—C— radical formers, radical formers with azo groups (—N=N—), radical formers with hydrazine groups (—NH—HN—), radical formers with hydrazone groups (>C=N—NH—), radical formers with azine groups (>C=N—N=C<), radical formers with triazene groups (—N=N—N<), radical formers with disulfide- or polysulfide groups (—S—S—), radical formers with thiol groups (—S—H), thiuram sulfide, dithiocarbamates, mercaptobenzothiazole, and sulphenamides.

12. The method according to claim 11, wherein the further radical former is selected from the group consisting of
a) N-alkoxyamines according to the structural formula

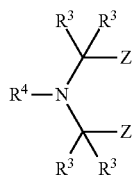

wherein
$R^3$ is hydrogen or an optionally substituted alkyl-, cycloalkyl-, aryl-, heteroaryl- or acyl-radical,
$R^4$ is an alkoxy-, aryloxy-, cycloalkoxy-, aralkoxy- or acyloxy-radical,
Z is hydrogen or an optionally substituted alkyl-, cycloalkyl-, aryl-, heteroaryl- or acyl-radical, or two Z radicals form a closed ring which is optionally substituted with an ester-, ether-, amine-, amide-, carboxy- or urethane-group,
b) azo compounds according to the structural formulae

$R^5$—N=N—$R^5$ or

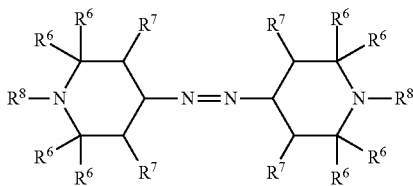

wherein
$R^5$ is an alkyl-, cycloalkyl- or aryl-radical,
$R^6$ upon each occurrence, is the same or different and is a linear or branched alkyl-radical,
$R^7$ upon each occurrence, is the same or different and is hydrogen or a linear or branched alkyl-radical, and
$R^8$ upon each occurrence, is the same or different and is an alkyl-, alkoxy-, aryloxy-, cycloalkyloxy-, aralkoxy or acyloxy-radical,
c) dicumylenes according to the structural formula

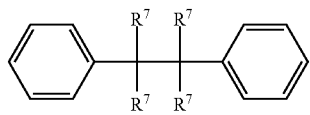

wherein $R^7$ has the previously indicated meaning, and
d) polycumylenes according to the structural formula

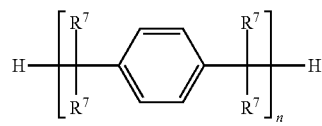

wherein $R^7$ has the previously indicated meaning and $2<n<100$.

13. The method according to claim 1, wherein the plastic materials are thermoplastic, elastomeric or duroplastic polymers.

14. The method according to claim 13, wherein the plastic materials are thermoplastic polymers.

15. The method according to claim 14, wherein the thermoplastic polymers are selected from the group consisting of
a) polymers made of olefins or diolefins,
b) polystyrene, polymethylstyrene, polyvinyl naphthalene, styrene-butadiene (SB), styrene-butadiene-styrene (SBS), styrene-ethylene-butylene-styrene (SEBS), styrene-ethylene-propylene-styrene, styrene-isoprene, styrene-isoprene-styrene (SIS), styrene-butadiene-acrylonitrile (ABS), styrene-acrylonitrile-acrylate (ASA), styrene-ethylene, and styrene-maleic anhydride polymers,
c) halogen-containing polymers,
d) polymers of unsaturated esters,
e) polymers made of unsaturated alcohols and derivatives,
f) polyacetals,
g) polyphenylene oxides and blends with polystyrene or polyamides,
h) polymers of cyclic ethers,
i) polyurethanes made of hydroxy-terminated polyethers or polyesters and aromatic or aliphatic isocyanates,
j) polyamides,
k) polyimides, polyamide imides, polyether imides, polyester imides, poly(ether)ketones, polysulphones, polyethersulphones, polyarylsulphones, polyphenylene sulphide, polybenzimidazoles, and polyhydantoins,
l) polyesters made of aliphatic or aromatic dicarboxylic acids and diols or made of hydroxycarboxylic acids,
m) polycarbonates, polyester carbonates, and blends thereof,
n) cellulose derivatives,
o) non-thermoplastic or duroplastic plastic materials, and
p) mixtures, combinations, or blends thereof.

16. The method according to claim 1, wherein the organic oxyimide is incorporated at a concentration of 0.01 to 30% by weight, relative to the plastic material.

17. The method according to claim 1, wherein the shaping is carried out by injection moulding or by extrusion.